US006444857B1

(12) United States Patent
Seko et al.

(10) Patent No.: US 6,444,857 B1
(45) Date of Patent: Sep. 3, 2002

(54) PROCESS FOR PRODUCING VITAMIN A ALDEHYDE AND INTERMEDIATE FOR PRODUCING THE SAME

(75) Inventors: Shinzo Seko, Toyonaka; Naoto Konya, Takatsuki; Toshiya Takahashi, Ibaraki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/684,922

(22) Filed: Oct. 10, 2000

(30) Foreign Application Priority Data

Oct. 12, 1999 (JP) ............................................ 11-289311

(51) Int. Cl.$^7$ ................................................ C07C 45/00
(52) U.S. Cl. ............................. 568/447; 568/31; 568/32
(58) Field of Search ............................. 568/31, 32, 447

(56) References Cited

U.S. PATENT DOCUMENTS

| 5,087,762 A | 2/1992 | Mori et al. |
| 5,118,866 A | 6/1992 | Knaus et al. |
| 6,211,411 B1 * | 4/2001 | Takahashi |
| 6,288,283 B1 * | 9/2001 | Seko |

FOREIGN PATENT DOCUMENTS

| EP | 900785 A3 | 3/1999 |
| EP | 0900785 A2 | 3/1999 |
| EP | 900785 A2 | 3/1999 |
| JP | 63233943 A | 9/1988 |
| JP | 7103095 B2 | 11/1995 |

OTHER PUBLICATIONS

F. Chemla et al., Bull. Soc. Chim. Fr., vol. 130, No. 2, pp. 200–205, XP002143691 (1993).
H. Bienayme, Tetrahedron Letters, vol. 35, No. 40, 1994, pp. 7383–7386.
P. Karrer et al., Helvetica Chimica Acta., vol. 40, No. 34, 1957, pp. 265–266.
Teruaki Mukaiyama et al., Chemistry Letters, 1975, pp. 1201–1202.
E.G.E. Hawkins et al., J.C.S., 1944, p. 411.
F. Chemla et al., Bull. Soc. Chim. Fr., vol. 130, 1993, pp. 200–205.

* cited by examiner

*Primary Examiner*—Michael L. Shippen
(74) *Attorney, Agent, or Firm*—Birch, Stewart, Kolasch & Birch, LLP

(57) ABSTRACT

There are disclosed an alcohol derivative of formula (1):

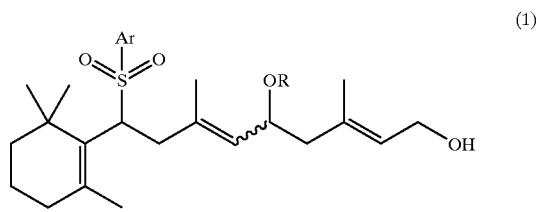

(1)

wherein Ar is an optionally substituted aryl group and R is a straight or branched C1–C3 lower alkyl group, and the wavy line depicted by

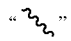

indicates a single bond and stereochemistry relating to a double bond bound therewith is E or Z or a mixture thereof, and a process for producing the same and a process for producing Vitamin A aldehyde using the same.

9 Claims, No Drawings

PROCESS FOR PRODUCING VITAMIN A ALDEHYDE AND INTERMEDIATE FOR PRODUCING THE SAME

BACKGROUND OF THE INVENTION

The present invention relates to a process for producing Vitamin A aldehyde, a key material for producing a carotenoid that is an important ingredient of pharmaceuticals, food and feed additives, and an intermediate for producing the same.

Vitamin A aldehyde is an important material for producing carotenoid such as β-carotene and a process of oxidizing retinol has been known for producing the same. However, the process has a drawback in that the process requires the use of retinol, which is very unstable to heat, light or oxygen.(e.g., J.Chem. Soc. 411 (1944), JP 63-233943A, Helv. Chim. Acta 40, 265 (1957), JP7-103095B).

There has also been known a carbon-increment reaction process at the side chain of C13 compounds such as β-ionone ( e.g., Tetrahedron Lett. 35, 7383 (1994)), or C10 compound cyclocitral (Chem. Lett. 1201 (1975)). These processes are not always advantageous from an industrial view point because commercially expensive β-ionone or cyclocitral and multistep processes are required. There has been also known a method in which a C10 cyclic sulfone compound is coupled with a C10 aldehyde dimethyl acetal compound having an allyl halide moiety in its molecule (Bull. Soc. Chim. Fr. 130, 200 (1993). The method is not always advantageous from industrial view point in that synthesis of said C10 aldehyde dimethyl acetal compound required multistep processes.

SUMMARY OF THE INVENTION

An object of the present invention is to provide a process for producing Vitamin A aldehyde using a novel intermediate which is easy to handle and readily available from a diol derivative of the formula (2) which is obtained from a rather inexpensive C10 compound such as linalool or geraniol or the like, without using unstable retinol.

DESCRIPTION OF THE PREFERRED EMBODIMENTS

The present invention provides:

1. An alcohol derivative of formula (1):

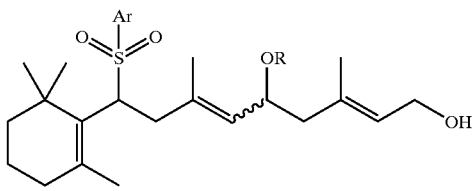

(1)

wherein Ar is an optionally substituted aryl group, R is a straight or branched C1–C3 lower alkyl group, and the wavy line depicted by

" ⁓ "

indicates a single bond and stereochemistry relating to a double bond bound therewith is E or Z or a mixture thereof;

2. A method for producing an alcohol derivative of formula (1) as defined above, which comprises reacting a diol derivative of formula (2):

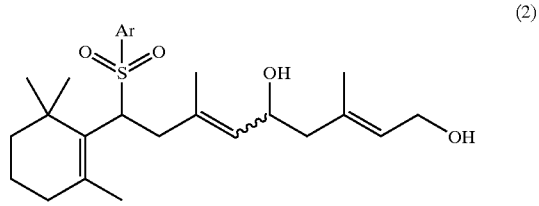

(2)

wherein Ar and the wavy line represent the same as defined above, with a lower alcohol of formula (3):

ROH    (3)

wherein R is a straight or branched C1–C3 lower alkyl group, in the presence of an acid catalyst; and 3. A method for producing an aldehyde derivative of formula (4):

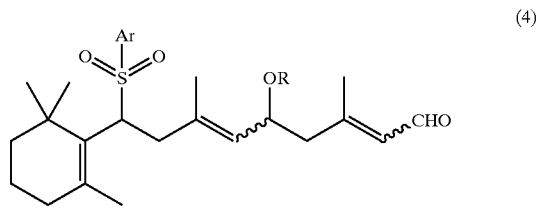

(4)

wherein Ar is an optionally substituted aryl group, R is a straight or branched C1–C3 lower alkyl group and the wavy line represents the same as defined above, which comprises reacting an alcohol derivative of formula (1) as defined above, with an oxidizing agent.

First, explanation will be made to the definitions of R and Ar in the chemical formulae (1), (2), (3) and (4) of the present specification.

Examples of the straight or branched C1–C3 alkyl group represented by R include a methyl, ethy, n-propyl and i-propyl group.

Examples of the optionally substituted aryl group represented by Ar include a phenyl group, a naphthyl group and the like, and the substituent which may be present on the said aryl groups includes a C1–C5 alkyl group (e.g., a methyl, ethyl, n-propyl, i-propyl, n-butyl, s-butyl, i-butyl, t-butyl, n-pentyl, neopentyl group, and the like), a C1–C5 alkoxy group (e.g., a methoxy, ethoxy, n-propoxy, i-propoxy, n-butoxy, s-butoxy, i-butoxy, t-butoxy, n-pentyloxy, neo-pentyloxy group, and the like), a halogen atom (e.g., a chlorine, bromine, fluorine or iodine atom), a nitro group and the like.

Specific examples thereof include phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl and the like.

Next a description will be made to the process for producing an alcohol derivative of formula (1), which comprises reacting a diol derivative of formula (2), with a lower alcohol of formula (3), in the presence of an acid catalyst.

The acid catalyst employed in this reaction includes a Lewis acid, and a Brønsted acid. Examples of the Lewis acid include stannous chloride, stannic chloride, zinc chloride, ferric chloride, boron trifluoride ether complex and a triflate of a rare earth element such as scandium triflate, and examples of the Brønsted acid include hydrobromic acid, hydrochloric acid, sulfuric acid, p-toluenesulfonic acid, benzenesulfonic acid, methanesulfonic acid, benzoic acid, triphenylphosphine hydrobromide, pyridine hydrochloride, a heteropolyacid such as phosphotungstic acid hydrate, phosphomolybdic acid hydrate or silicotungstic acid hydrate and the acidic ion exchange resin such as a strongly acidic resin having a terminal sulfonic acid group.

The amount of an acid catalyst is usually 0.01 to 3 moles per mol of the diol derivative of formula (2).

Examples of the lower alcohol include methanol, ethanol, n-propanol, and i-propanol and the like.

Preferred are methanol, ethanol and i-propanol.

These alcohols can be usually used as a solvent.

The reaction temperature usually ranges from −78° C. to the boiling point of the solvent employed, and preferably from −10° C. to 50° C.

After completion of the reaction, the alcohol derivative (1) is usually isolated by a conventional post treatment such as extraction, evaporation, and /or recrystallization, and may be further purified by chromatography on a silica gel, if necessary.

Specific examples of the alcohol derivative of formula (1) include an alcohol compound of formula (1), wherein R is a methyl group and Ar is a tolyl group, and further alcohol compounds of formula (1), wherein R is an ethyl, n-propyl, i-propyl group in place of the methyl group in the above-described compound and alcohol compounds of formula (1), wherein Ar represents a phenyl, naphthyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, or p-nitrophenyl group in place of the tolyl group in the above-described compounds.

The aldehyde derivative (4) can be obtained by a method which comprises reacting the alcohol derivative of formula (1) with an oxidizing agent optionally in the presence of a catalyst. Examples of the oxidizing agent and the optionally used catalyst will be specified as below.

The oxidizing of the alcohol derivative (1) is usually conducted by one of the following methods and the like.

The oxidizing of the alcohol derivative (1) can be conducted by a step comprising:

(a) subjecting the alcohol derivative (1) to contact with a metal oxidant, or (b) subjecting the alcohol derivative (1) to contact with a sulfoxide compound, a sulfoxide-activating compound and optionally a base, or (c) subjecting the alcohol derivative (1) to contact with a sulfide compound, a halogenating agent and a base, or (d) subjecting the alcohol derivative (1) to contact with an aldehyde in the presence of a catalyst selected from an aluminum alkoxide or aryloxide, and a boron compound, or (e) subjecting the alcohol derivative (1) to contact with an oxygen in the presence of a catalyst.

A description will be made to the oxidizing step (a).

Examples of the metal oxidant include a salt or oxide of chromium or manganese, an oxide of nickel or selenium, or a salt of silver. Specific examples thereof include pyridinium chlorochromate, pyridinium dichromate, manganese dioxide, nickel peroxide, selenium dioxide and silver carbonate. The amount of the metal oxidant to be used is usually about 1 to 20 moles, preferably 1 to 10 moles per mol of the alcohol derivative (1).

The reaction is usually conducted in a solvent. Examples of the solvent include a hydrocarbon solvent such as n-hexane, cyclohexane, n-pentane, n-heptane, toluene or xylene, a halogenated hydrocarbon solvent such as chloroform, dichloromethane, 1,2-dichloroethane, monochlorobenzene, o-dichlorobenzene or α,α,α-trifluorotoluene, an aprotic polar solvent such as N,N-dimethylformamide, dimethylsulfoxide, acetonitrile, N,N-dimethylacetamide or hexamethylphosphoric triamide or an ether solvent such as 1,4-dioxane, tetrahydrofuran or anisole. The reaction temperature is usually in a range between about 0° C. and 50° C.

After completion of the reaction, the reaction mixture is usually subjected to post-treatments which include filtration to remove the metal oxidant where an organic solvent as listed above or water may be optionally used, phase separation, washing and/or evaporation to give the desired product, which may be further purified by column chromatography or recrystallization, if necessary.

Next, a description will be made to the oxidizing reactions (b) and (c) described above, which may be referred to as "Swern oxidation" or "Corey-Kim oxidation" respectively.

Examples of the sulfoxide compound include a di(C1–C3)alkyl sulfoxide such as dimethylsulfoxide and the like. Examples of the sulfoxide-activating compound include oxalyl chloride, acetic anhydride, thionyl chloride, phosgene or the like. The sulfoxide compound and the sulfoxide-activating compound are usually used in an equimolar amount each other. Specific examples of the combination thereof include dimethylsulfoxide and oxalyl chloride, dimethylsulfoxide and any one of the above-described sulfoxide-activating compound other than oxalyl chloride and the like.

Examples of the sulfide compound include a methyl (C1–C3)alkyl sulfide or methylphenylsulfide such as dimethylsulfide and the like. Examples of the halogenating agent to be used with the sulfide compound include N-chlorosuccinimide and the like. The sulfide compound and the halogenating agent are usually used in an equimolar amount each other. Specific examples of the combination thereof include dimethylsulfide and N-chlorosuccinimide, and the like.

The amount of the sulfoxide compound and sulfoxide-activating compound, or the sulfide compound and halogenating agent to be used is usually about 1 to 5 moles, preferably about 1 to 3 moles per mol of the alcohol derivative (1).

Examples of the base include a (C6–C12)tertiary amine such as triethylamine, tripropylamine or tributylamine. The amount of the base is usually about 1 to 5 moles, preferably 1 to 3 moles per mol of the sulfoxide compound or the sulfide compound.

The reaction is usually conducted in a solvent, examples of which include those described for the oxidizing reaction (a) above and an ester solvent such as ethyl acetate or butyl acetate. The reaction temperature is usually in a range of about −80 to 0° C.

Next a description will be made to the reaction (d), which may be referred to as a hydrogen transfer type oxidation reaction (for example, Oppenauer oxidation).

Examples of the aluminum alkoxide or aryloxide to be used in this reaction include a (C3–C7) secondary or tertiary alkoxide or aryloxide of aluminum.

Specific examples thereof include aluminum isopropoxide, aluminum t-butoxide, aluminum s-butoxide and aluminum phenoxide. Examples of the boron compounds include tris(pentafluorophenyl) boron and bis(pentafluorophenyl)boric acid.

Examples of the aldehyde, as a hydrogen acceptor, include a tertiary alkyl or aromatic aldehyde having C5–C7 carbon atoms such as trimethylacetaldehyde, 2,2-dimethylbutanal or benzaldehyde.

The amount of the aluminum alkoxide or aryloxide, or boron compounds may be catalytic and is usually about 0.001 to 0.3 mol, preferably about 0.01 to 0.1 mol per mol of the alcohol derivative (1).

The amount of the aldehyde is usually about 1 to 10 moles, preferably about 1 to 5 moles per mol of the alcohol derivative (1).

The reaction is usually conducted in a solvent, examples of which include those described for the oxidizing reaction (a) above. The reaction temperature is usually in a range of about 10 to 60° C.

Next a description will be made to the oxidation reaction (e).

Examples of the catalyst for the oxidation reaction using oxygen include platinum, a catalyst comprising 2,2,6,6-tetramethylpiperidine 1-oxyl (TEMPO) and copper chloride, a catalyst comprising tris(triphenylphosphine)ruthenium and hydroquinone, and a catalyst comprising tetrapropylammonium perruthenate and molecular sieves 4A.

The amount of the catalyst to be used is usually about 0.001 to 0.3 mol, preferably about 0.01 to 0.1 mol per mol of the alcohol derivative (1). The reaction is usually conducted in a solvent, examples of which include those described for the oxidizing reaction (a) above.

Oxygen may be used either alone or as a mixture with other gases such as air, and it may be either of atmospheric pressure or pressured and may be introduced into the reaction solution. The reaction temperature is usually in a range of about 10° C. to 60° C.

After completion of the above-described reactions of (b) to (e), the reaction mixture is usually subjected to post-treatments which include optionally filtration, washing, phase separation and/or evaporation as described above for the step (a) to give the desired products, which may be further purified by column chromatography or recrystallization, if necessary.

Specific examples of the aldehyde derivative of the formula (4) include following compounds such as an aldehyde derivative of formula (4), wherein R and Ar respectively represent the same group as specified for the alcohol derivative of formula (1) above.

The aldehyde derivative (4) thus obtained can be derivatized to retinal by contacting the aldehyde derivative of formula (4) with a base.

Examples of the base to be used include an alkali metal hydroxide such as sodium hydroxide, potassium hydroxide, lithium hydroxide or the like, an alkali metal hydride such as sodium hydride, potassium hydride or the like, an alkali metal alkoxide such as sodium methoxide, potassium methoxide, sodium ethoxide, potassium ethoxide, sodium t-butoxide, potassium t-butoxide or the like, a bicyclic tertiary amine compound such as 1,8-diazabicyclo[5.4.0]undec-7-ene (DBU) and 1,5-diazabicyclo[4.3.0]non-5-ene(DBN), a proazaphosphatrane and 1,8-bis(dimethylamino) naphthalene and the like.

Preferred are the bicyclic tertiary amine compound, proazaphosphatrane and 1,8-bis(dimethylamino) naphthalene and the like.

The amount of the base is usually 0.1 mole to 20 moles per mole of the aldehyde derivative of formula (4). Alternatively, the above-described base may be used in a catalytic amount together with one equivalent or more of an alkali metal carbonate such as potassium carbonate or sodium carbonate.

The reaction of the aldehyde derivative (4) with the base is usually conducted in an organic solvent. Examples of the solvent include an ether such as 1,4-dioxane, tetrahydrofuran, anisole and the like, a hydrocarbon solvent such as n-hexane, n-heptane, cyclohexane, n-pentane, toluene, xylene and the like, a halogenated solvent such as chloroform, dichloromethane, 1,2-dichloroethane, monochlorobenzene, o-dichlorobenzene and the like, an aprotic polar solvent such as acetonitrile, N,N-dimethylformamide, dimethylsulfoxide, N,N-dimethylacetamide, hexamethylphosphoric triamide and the like.

The reaction temperature usually ranges from −30° C. to the boiling point of the solvent employed, preferably 20° C. to 100° C.

After completion of the reaction, Vitamin A aldehyde is usually isolated by a conventional post treatment such as extraction, and evaporation, and may be further purified by chromatography on a silica gel, if necessary.

The diol derivative (2) can be readily produced by a method as shown in Scheme 1 below form inexpensive geraniol or linalool.

The preparation method of the cyclic sulfone (5) is disclosed in Chem. Lett., 479 (1975) and that of sulfone derivative (6) is disclosed in JP11-222479A(Laid-open). The diol derivative of formula (2) can be readily obtained by hydrolyzing sulfone compound of formula (6).

Scheme 1

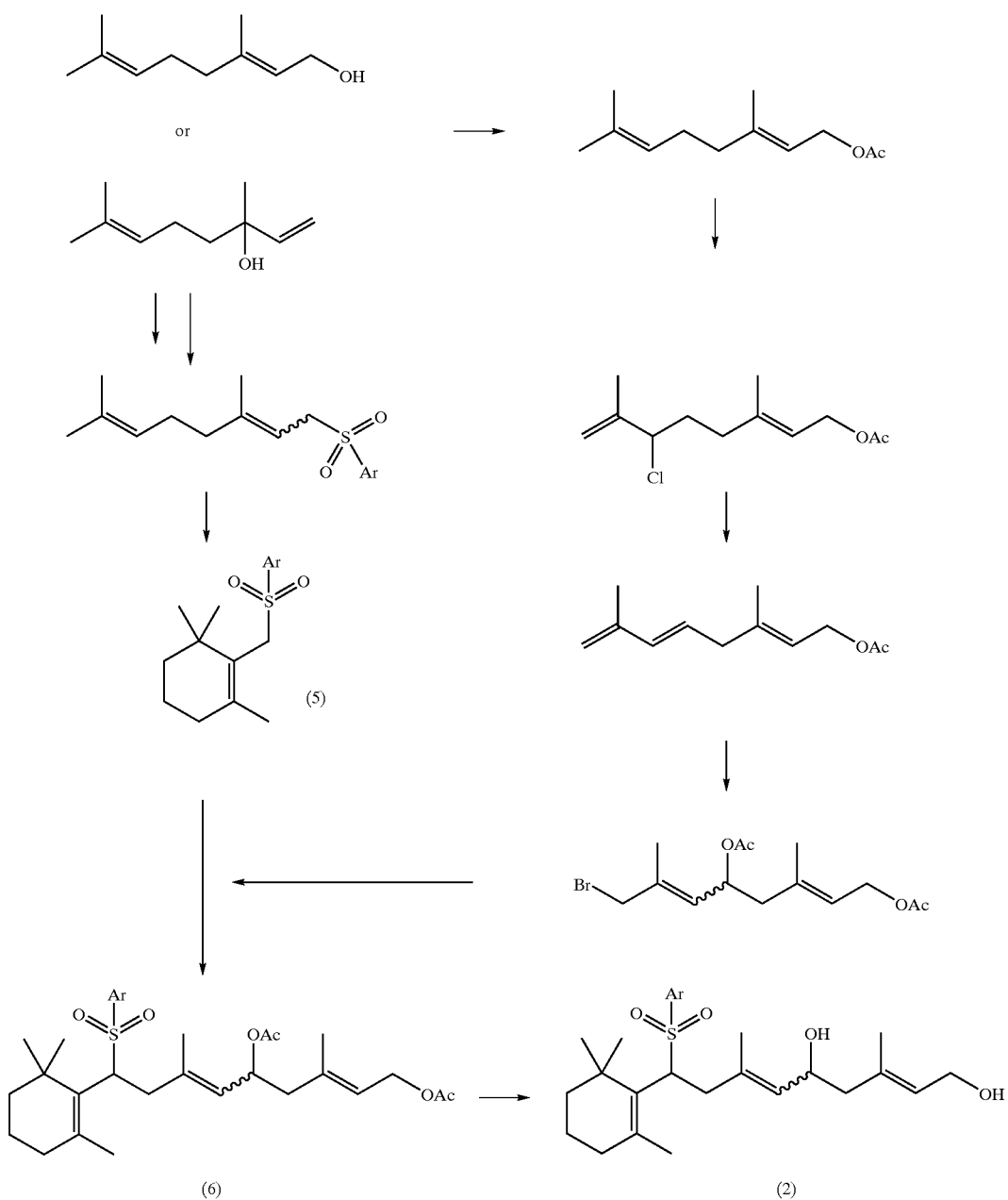

The diol derivative of formula (2) may be E-isomer, Z-isomer or a mixture thereof or may be a optically active isomer, diastereomers or a racemate.

According to the method of the present invention, Vitamin A aldehyde can be produced by using a readily available diol derivative of formula (2), which can be obtained from a rather inexpensive C10 compound such as linalool or geraniol or the like, without using unstable retinol.

EXAMPLES

The present invention is further described in the following examples which are not intended to restrict the invention. In the following examples, compounds are designated by the corresponding Roman characters and the chemical structures are shown in the FIG. 1 below.

Example 1

5.48 g (11.9 mmol) of Diol compound (I) were dissolved in 50 ml of methanol and then 114 mg (0.6 mmol) of p-toluenesulfonic acid was added thereto. After stirring at room temperature for 24 hours, 114 mg (0.6 mmol) of p-toluenesulfonic acid was further added thereto and stirred at room temperature for 24 hours. After completion of the reaction, saturated aqueous sodium hydrogen carbonate solution was added to the reaction mixture and extracted with ether. The organic layer was washed with saturated aqueous sodium chloride solution, and dried over anhydrous magnesium sulfate. The solvent was evaporated and to give a crude product, which was purified by a silica gel column chromatography to give Methoxy alcohol (II) as a pale yellow oil (a mixture of E and Z isomers and diastereomers) in 76% yield.

$^1$H-NMR δ(CDCl$_3$) 0.70–1.10(6H,m), 1.30–1.65(8H,m), 1.65–1.75(3H,br), 1.90–2.40(6H,m), 2.44(3H,s), 2.60–2.80 (1H,m), 2.90–3.15(1H,m), 3.15–3.25(3H,m), 3.80–4.00(2H, m), 4.00–4.20(2H,m), 5.00–5.20(1H,m), 5.35–5.50(1H,m), 7.20–7.40(2H,m), 7.70–7.90(2H,m).

Example 2

1.42 g (2.99 mmol) of Methoxy alcohol (II) were dissolved in 10 ml of dichloromethane and then 1.3 g of manganese dioxide was added thereto. After stirring at room temperature for 8 hours, 1.3 g of manganese dioxide was further added thereto and stirred for 12 hours. Then the reaction mixture was diluted with ether, dried over anhydrous magnesium sulfate, filtered and evaporated to remove the solvent to give a crude product, which was purified by a silica gel column chromatography to obtain Methoxy aldehyde (III) as a pale yellow oil, which contains E, Z-isomers and diastereomers, in 91% yield.

$^1$ H-NMR δ(CDCl$_3$) 0.75–1.05(6H,m), 1.30–1.60(8H,m), 1.90–2.45(3H,m), 2.02(3H,d, J=1.5 Hz), 2.18(3H,t,J=1.5 Hz), 2.45(3H,s), 2.71(1H,dd,J=7 Hz,15 Hz), 3.04(1H,dd,J=6 Hz,15 Hz) 3.18(3H,d, J=15 Hz), 3.85–3.95(1H,m), 3.95–4.05(1H,m), 5.00–5.10(1H,m), 5.80–5.90(1H,m), 7.20–7.35(2H,m), 7.65–7.85(2H,m), 9.98(1H,d, J=8 Hz).

Example 3

1.035 g (2.19 mmol) of Methoxy aldehyde (III) was dissolved in a mixed solvent of 5 ml of acetonitrile and 5 ml of dichloromethane and then 2.66 g (17.5 mmol) of DBU was added thereto, and the resulting mixture was refluxed for 6 hours. After the reaction, water was added to the reaction mixture and extracted with ether. The organic layer was washed with saturated aqueous sodium chloride solution and dried over anhydrous magnesium sulfate. Then the filtered solution was evaporated to give a crude Vitamin A aldehyde in 48 % yield.

Example 4

958 mg (2.08 mmol) of Diol compound (I) was dissolved in 10 ml of isopropanol, and 20 mg (0.2 mmol) of 96% sulfuric acid was added thereto. After stirring at room temperature for 24 hours, 100 mg (1.0 mmol) of 96% sulfuric acid was further added thereto and stirred for 24 hours at room temperature. After completion of the reaction, saturated aqueous sodium hydrogen carbonate was added to the reaction mixture and extracted with ether. The organic layer was washed with saturated aqueous sodium chloride solution and dried over anhydrous magnesium sulfate. The solvent was evaporated to give a crude product, which was purified by silica gel column chromatography to give Isopropoxy alcohol (IV) as a pale yellow oil containing E, Z-isomers, and diastereomers in 42 % yield.

$^1$H-NMR δ(CDCl$_3$) 0.70–1.00(6H,m), 1.05–1.07(6H,m), 1.30–1.65(8H,m), 1.68(3H,br), 1.85–2.30(6H,m), 2.44(3H, s), 2.60–2.80(1H,m), 2.90–3.15(1H,m), 3.40–3.60(1H,m), 3.80–4.00(1H,m), 4.00–4.20(3H,m), 5.00–5.20(1H,m), 5.35–5.50(1H,m), 7.20–7.40(2H,m), 7.70–7.90(2H,m).

Example 5

375 mg (0.75 mmol) of Isopropoxy alcohol (IV) was dissolved in 5 ml of dichloromethane, and 0.33 g of manganese dioxide was added thereto. The mixture was stirred at room temperature for 8 hours. After 0.32 g of manganese dioxide was further added thereto and stirred at room temperature for 12 hours, the reaction solution was diluted with ether. Filtrate was dried over anhydrous magnesium sulfate, and filtrate was evaporated to give a crude product, which was further purified by silica gel column chromatography to give Isopropoxy aldehyde (V) as a mixture of a pale yellow oil of E,Z-isomers and diastereomers in 80% yield.

$^1$H-NMR δ(CDCl$_3$) 0.70–1.00(6H,m), 1.00–1.15(6H,m), 1.30–1.65(8H,m), 1.90–2.15(6H,m), 2.15–2.25(3H ,m), 2.45(3H,s), 2.72(1H, dd, J=7 Hz, 15 Hz), 2.97(1H,dd, J=5 Hz, 15 Hz), 3.30–3.60(1H,m), 3.80–4.00(1H,m), 4.00–4.40 (1H,m), 5.00–5.20(1H,m), 5.80–6.00(1H,m), 7.20–7.35(2H, m), 7.65–7.85(2H, m), 9.82–10.02(1H,).

Example 6

100 mg (0.2 mmol) of Isopropoxy aldehyde (V) was dissolved in a mixed solvent of 1 ml of acetonitrile and 1 ml of dichloromethane and 152 mg (1.0 mmol) of DBU was added thereto and refluxed for 5.5 hours. The reaction mixture was evaporated to give a crude product, which was purified by a silica gel column chromatography to give Vitamin A aldehyde in 41% yield.

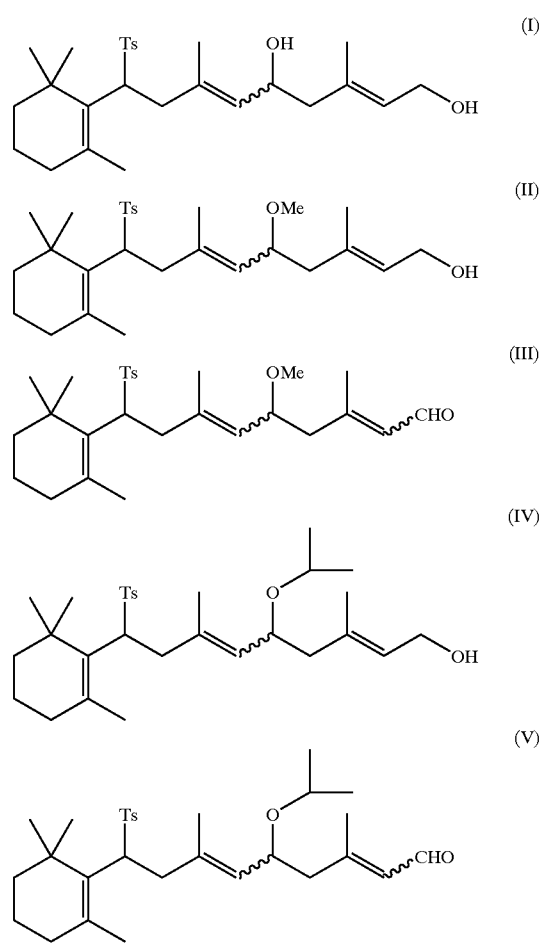

Ts: p-Tolylsulfonyl group.
FIG. 1

What is claimed is:
1. A method for producing an alcohol derivative of formula (1):

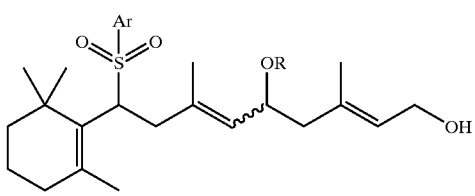
(1)

wherein
Ar is an aryl group, which may be substituted with a substituent group selected from
a C1–C5 alkyl group, a C1–C5 alkoxy group, a halogen atom and a nitro group,
R is a straight or branched C1–C3 lower alkyl group, and the wavy line depicted by

indicates a single bond and stereochemistry relating to a double bond bound therewith is E or Z or a mixture thereof,
which comprises reacting a diol derivative of formula (2):

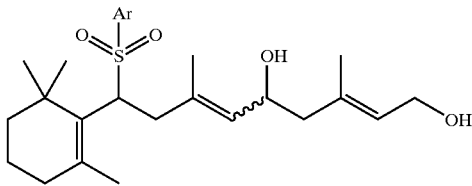
(2)

wherein Ar and the wavy line represent the same as defined above, with a lower alcohol of formula:

ROH  (3)

wherein R is a straight or branched C1–C3 lower alkyl group, in the presence of an acid catalyst.

2. A method for producing an aldehyde derivative of formula (4):

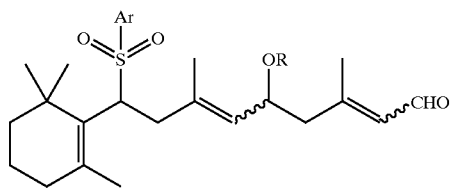
(4)

wherein
Ar is an aryl group, which may be substituted with a substituent group selected from
a C1–C5 alkyl group, a C1–C5 alkoxy group, a halogen atom and a nitro group,
R is a straight or branched C114 C3 lower alkyl group, and the wavy line depicted by

indicates a single bond and stereochemistry relating to a double bond bound therewith is E or Z or a mixture thereof, which comprises reacting an alcohol derivative of formula (1):

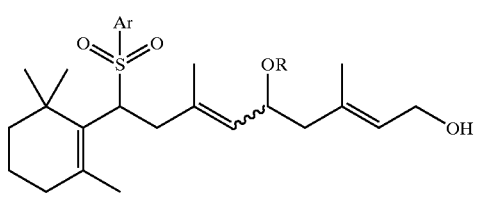
(1)

wherein Ar, R and the wavy line represent the same as defined above, with an oxidizing agent optionally in the presence of a catalyst.

3. A method according to claim 2, which further comprises the step of reacting said aldehyde derivative of formula (4), with a base to produce Vitamin A aldehyde of formula (5):

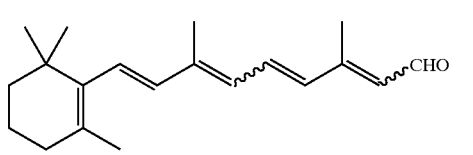
(5)

wherein the wavy line depicted by "" indicates a single bond and stereochemistry relating to a double bond bound therewith is E or Z or a mixture thereof.

4. A method for producing Vitamin A aldehyde of formula (5):

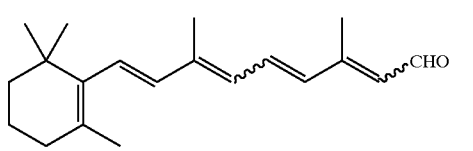
(5)

wherein the wavy line depicted by

"  "

indicates a single bond and stereochemistry relating to a double bond bound therewith is E or Z or a mixture thereof, which comprises the steps of:

reacting a diol derivative of formula (2):

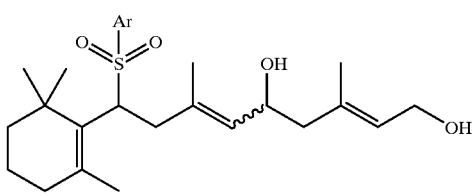
(2)

wherein
Ar is an aryl group, which may be substituted with a substituent group selected from
a C1–C5 alkyl group, a C1–C5 alkoxy group, a halogen atom and a nitro group, and the wavy line represents the same as defined above, with a lower alcohol of formula:

ROH (3)

wherein R is a straight or branched C1–C3 lower alkyl group, in the presence of an acid catalyst, to produce an alcohol derivative of formula (1):

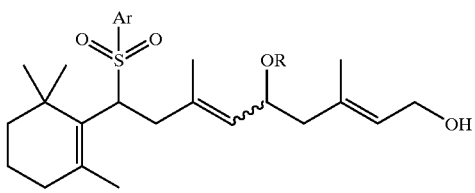
(1)

wherein Ar, R and the wavy line represent the same as defined above,
reacting the alcohol derivative of formula (1) with an oxidizing agent optionally in the presence of a catalyst to produce an aldehyde derivative of formula (4):

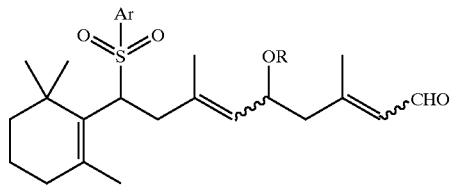
(4)

wherein Ar, R and the wavy line represent the same as defined above, and reacting the aldehyde derivative of formula (4) with a base.

5. A method according to claim 1 or 4, wherein said acid catalyst is a Lewis acid or a Brønsted acid.

6. A method according to claim 1 or 4, wherein said acid catalyst is stannous chloride, stannic chloride, zinc chloride, ferric chloride, boron trifluoride ether complex, scandium triflate, hydrogen bromide, hydrogen chloride, sulfuric acid, p-toluenesulfonic acid, benzenesulfonic acid, methanesulfonic acid, benzoic acid, triphenylphosphine hydrobromide, pyridine hydrochloride, phosphotungstic acid hydrate, phosphomolybdic acid hydrate, silicotugstic acid hydrate, or an acidic ion exchange resin having a terminal sulfonic acid group.

7. A method according to claim 2, or 4 wherein said oxidizing of the alcohol derivative of formula (1) comprises:
(a) subjecting the alcohol derivative (1) to contact with a metal oxidant, or
(b) subjecting the alcohol derivative (1) to contact with a sulfoxide compound, a sulfoxide-activating compound and optionally a base, or
(c) subjecting the alcohol derivative (1) to contact with a sulfide compound, a halogenating agent and a base, or
(d) subjecting the alcohol derivative (1) to contact with an aldehyde in the presence of a catalyst selected from an aluminum alkoxide or aryloxide, and a boron compound, or
(e) subjecting the alcohol derivative (1) to contact with an oxygen in the presence of a catalyst selected from
platinum, a catalyst comprising 2,2,6,6-tetramethylpiperidine 1-oxyl and copper chloride, a catalyst comprising tris(triphenylphosphine) ruthenium and hydroquinone chloride, and a catalyst comprising tetrapropylammonium perruthenate and molecular sieves 4A.

8. A method according to claim 3 or 4, wherein said base is an alkali metal hydroxide, an alkali metal hydride, an alkali metal alkoxide, a bicyclic tertiary amine compound, proazaphosphatrane and 1,8-bis(dimethylamino) naphthalene.

9. A method according to claim 3 or 4, wherein the base is sodium hydroxide, potassium hydroxide, lithium hydroxide, sodium hydride, potassium hydride, sodium methoxide, potassium methoxide, sodium ethoxide, potassium ethoxide, sodium t-butoxide, potassium t-butoxide, 1,8-diazabicyclo[5.4.0]undec-7-ene, 1,5-diazabicyclo[4.3.0]non-5-ene, proazaphosphatrane or 1,8-bis(dimethylamino) naphthalene.

* * * * *